US010390973B2

(12) United States Patent
Tong et al.

(10) Patent No.: US 10,390,973 B2
(45) Date of Patent: Aug. 27, 2019

(54) INTERACTIVE EXOSKELETON ROBOTIC KNEE SYSTEM

(71) Applicant: THE HONG KONG POLYTECHNIC UNIVERSITY, Hong Kong (HK)

(72) Inventors: Kai-Yu Tong, Hong Kong (HK); Corinna Ursula Ockenfeld, Hong Kong (HK); Ling Fung Yeung, Hong Kong (HK); Sze Kit Ho, Hong Kong (HK); Hon-Wah Wai, Hong Kong (HK); Man-Kit Pang, Hong Kong (HK)

(73) Assignee: THE HONG KONG POLYTECHNIC UNIVERSITY, Hong Kong (HK)

( * ) Notice: Subject to any disclaimer, the term of this patent is extended or adjusted under 35 U.S.C. 154(b) by 481 days.

(21) Appl. No.: 14/745,462

(22) Filed: Jun. 21, 2015

(65) Prior Publication Data

US 2016/0331560 A1 Nov. 17, 2016

Related U.S. Application Data

(60) Provisional application No. 62/159,951, filed on May 11, 2015.

(51) Int. Cl.
*A61F 2/70* (2006.01)
*A61F 2/64* (2006.01)
(Continued)

(52) U.S. Cl.
CPC .............. *A61F 2/70* (2013.01); *A61B 5/1038* (2013.01); *A61B 5/112* (2013.01); *A61B 5/1121* (2013.01);
(Continued)

(58) Field of Classification Search
CPC .... A61H 1/024; A61H 3/00; A61H 2201/165; A61H 2201/164; A61H 2201/1463;
(Continued)

(56) References Cited

U.S. PATENT DOCUMENTS 3,449,769 A 6/1969 Mizen
3,553,738 A 1/1971 Theodore
(Continued)

FOREIGN PATENT DOCUMENTS

CN 102574285 A 7/2012
CN 103006362 A 4/2013
(Continued)

OTHER PUBLICATIONS

Archived: Jan. 28, 2008; retrieved: Sep. 12, 2017; website: http://www.sciencedirect.com/science/article/pii/S0007850607614176.*
(Continued)

*Primary Examiner* — Megan Anderson
(74) *Attorney, Agent, or Firm* — Spruson & Ferguson (Hong Kong) Limited

(57) ABSTRACT

An interactive exoskeleton robotic knee system for assist walking and gait training. The system comprises of an exoskeleton framework to be attached to the thigh and shank of the user's leg; electric motor; mechanical lock; motion sensor assembled on the lower limb unit, and a control box. The system provides extension and flexion movement in the knee joint.

16 Claims, 12 Drawing Sheets

(51) Int. Cl.
  *A61H 3/00* (2006.01)
  *A61B 5/11* (2006.01)
  *A61B 5/00* (2006.01)
  *A61B 5/103* (2006.01)
  *A61H 1/02* (2006.01)

(52) U.S. Cl.
  CPC .......... *A61B 5/1123* (2013.01); *A61B 5/6812* (2013.01); *A61B 5/6828* (2013.01); *A61F 2/64* (2013.01); *A61H 1/024* (2013.01); *A61H 3/00* (2013.01); *A61B 2562/0219* (2013.01); *A61B 2562/0252* (2013.01); *A61H 2201/1207* (2013.01); *A61H 2201/1215* (2013.01); *A61H 2201/1463* (2013.01); *A61H 2201/164* (2013.01); *A61H 2201/165* (2013.01); *A61H 2201/1676* (2013.01); *A61H 2201/5007* (2013.01); *A61H 2201/5069* (2013.01); *A61H 2201/5079* (2013.01); *A61H 2201/5084* (2013.01); *A61H 2201/5097* (2013.01)

(58) Field of Classification Search
  CPC .... A61H 2201/1207; A61H 2201/5007; A61H 2201/1676; A61H 2201/5097; A61H 2201/5069; A61H 2201/5079; A61H 1/02; A61H 1/0237; A61H 1/0244; A61H 1/0262; A61H 2203/04; A61H 2203/0406; A61H 2205/10; A61H 2205/102; A61H 2205/106; A61H 2201/1215; A61H 2201/00; A61H 2201/0157; A61H 2201/0173; A61H 2201/0176; A61H 2201/018; A61H 2201/12; A61H 2201/1642; A61H 2201/15; A61H 2201/5058; A61H 2201/5061; A61H 2201/5064; A61H 2201/5071; A61H 2201/5084; A61B 5/1038; A61B 5/1121; A61B 5/1123; A61B 5/6812; A61B 5/6828; A61B 5/112; A63B 3/00
  See application file for complete search history.

(56) References Cited

U.S. PATENT DOCUMENTS

| | | | |
|---|---|---|---|
| 6,834,752 B2 | 12/2004 | Irby et al. | |
| 6,867,685 B1 | 3/2005 | Stillwagon | |
| 6,955,692 B2 | 10/2005 | Grundei | |
| 7,190,141 B1 | 3/2007 | Ashrafiuon et al. | |
| 7,393,335 B2 | 7/2008 | Carvey et al. | |
| 7,731,670 B2 | 6/2010 | Ollinberg A et al. | |
| 7,774,177 B2 | 8/2010 | Dariush et al. | |
| 7,947,004 B2 | 5/2011 | Kazerooni et al. | |
| 8,057,410 B2 | 11/2011 | Angold et al. | |
| 8,096,965 B2 | 1/2012 | Goffer et al. | |
| 8,623,098 B2 | 1/2014 | Goldfarb et al. | |
| 8,679,040 B2 | 3/2014 | Horst et al. | |
| 9,211,201 B2 * | 12/2015 | Herr | A61F 2/60 |
| 9,345,592 B2 * | 5/2016 | Herr | A61F 2/60 |
| 9,445,931 B2 * | 9/2016 | Imaida | A61F 5/01 |
| 9,554,922 B2 * | 1/2017 | Casler | A61F 2/60 |
| 9,566,705 B2 * | 2/2017 | Goldfarb | A61H 1/024 |
| 2009/0043357 A1 * | 2/2009 | Tong | A61B 5/112 607/49 |
| 2010/0125229 A1 | 5/2010 | Rudolph et al. | |
| 2010/0241242 A1 | 9/2010 | Herr et al. | |
| 2010/0256537 A1 | 10/2010 | Menga | |
| 2011/0040216 A1 | 2/2011 | Herr et al. | |
| 2011/0066088 A1 | 3/2011 | Little et al. | |
| 2011/0264014 A1 | 10/2011 | Angold | |
| 2011/0266323 A1 | 11/2011 | Kazerooni et al. | |
| 2013/0102934 A1 * | 4/2013 | Ikeuchi | A61H 3/00 601/35 |
| 2013/0190669 A1 | 7/2013 | Rokosz et al. | |
| 2013/0226048 A1 | 8/2013 | Unluhisarcikli et al. | |
| 2013/0253385 A1 | 9/2013 | Goffer et al. | |
| 2013/0296741 A1 * | 11/2013 | Wiggin | A61B 5/112 600/595 |
| 2013/0296746 A1 | 11/2013 | Herr et al. | |
| 2014/0100493 A1 | 4/2014 | Craig et al. | |
| 2014/0172168 A1 | 6/2014 | Lee et al. | |
| 2014/0200491 A1 | 7/2014 | Julin et al. | |
| 2014/0276304 A1 | 9/2014 | Dollar et al. | |
| 2015/0025423 A1 * | 1/2015 | Caires | A61H 1/024 601/35 |
| 2015/0173929 A1 * | 6/2015 | Kazerooni | A61F 5/0125 602/16 |
| 2015/0190249 A1 * | 7/2015 | Ishibashi | A61H 3/00 623/24 |
| 2015/0196403 A1 * | 7/2015 | Kim | A61F 2/70 623/24 |
| 2016/0095538 A1 * | 4/2016 | Lee | A61B 5/7267 600/595 |
| 2016/0270997 A1 * | 9/2016 | Little | A61H 3/00 |
| 2017/0128311 A1 * | 5/2017 | Lee | F16H 19/06 |

FOREIGN PATENT DOCUMENTS

| | | |
|---|---|---|
| CN | 103260576 A | 8/2013 |
| CN | 103356363 A | 10/2013 |
| CN | 104582668 A | 4/2015 |

OTHER PUBLICATIONS

Translation of CN 103610569.*
Office Action of Taiwan Application No. 105113882 issued from the Taiwan Intellectual Property Office dated Jul. 11, 2017.
2nd Office Action of Taiwan Application No. 105113882 issued from the Taiwan Intellectual Property Office dated Apr. 10, 2018.

* cited by examiner

INTERACTIVE EXOSKELETON ROBOTIC KNEE SYSTEM

CROSS REFERENCE TO RELATED APPLICATION

Pursuant to 35 U.S.C. § 119(e), this is a non-provisional patent application which claims benefit from U.S. provisional patent application Ser. No. 62/159,951 filed May 11, 2015, and the disclosure of which is incorporated herein by reference.

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The invention concerns a wearable interactive device to power assist the user's locomotion by moving the knee joint or providing supportive force on the knee joint. In particular, the present intervention relates to a gait assistive training device and method.

BACKGROUND

Powered exoskeleton rehabilitation devices have been proposed to assist the user's locomotion providing supportive force on the knee joint such as weight bearing. However, most of the current devices suffer from bulky and heavy design, a lack of active interaction between user and device, intuitive adjustment to the environment and pre-programmed walking trajectory.

Gait abnormality in the knee joint are very common among elders and post-stroke patients. Stroke is one of the primary causes of long-term disabilities, which affect their independency and the walking ability. Stroke may result in knee instability coupled with hyperextension. It is characterized by an extension of the knee joint beyond the neutral position, which could either occur rapid and abrupt or slowly during the gait cycle. Patients with a hyperextension acquire an abnormal gait pattern, which can increase the energy expenditure, reduce the ability to balance and can lead to pain, capsular and ligamentous laxity and/or bone deformity.

Another effect is the resulting adduction moment during the gait adaption, which increase the lateral distraction forces on the medial tibiofemoral unit. This can lead to pain in the medial tibiofemoral and/or posterolateral soft tissues and/or can lead to abnormal tibiofemoral alignments such as varus malalignment or anterior-posterior tibial slope. Other secondary medical problems of genu recurvatum are: joint contractures, osteoporosis, and pressure ulcer.

The normal gait pattern requires an adequate push-off by the gastrocnemius and soleus, a sufficient contraction of the quadriceps during the midstance, flexion of the hip and knee joint during the swing phase, and good balance and posture. Therefore, an effective gait recovery should incorporate those specific requirements in order to avoid an abnormal gait pattern or a hyperextension gait mechanism.

Gait recovery could be achieved by several rehabilitation means. In orthotics approach, stroke patients could be prescribed with lightweight knee-ankle-foot orthosis (KAFO) that can stabilize the knee and ankle joint. However, the training effect of the KAFO is limited. Physiotherapy (PT) and occupational therapy (OT) on the other hand are common interventions to enhance motor functions and slow down the progression of impaired mobility. Traditional therapy techniques include gait training, such as; overground, treadmill, motor relearning program, proprioceptive neuromuscular facilitation techniques, and Bobath-method. Previous studies showed that although these rehabilitation programs could reduce the severity of neuromuscular impairments, the effects were not task-specific, were limited to the targeted area only, and patients tend to adapt to compensatory strategies instead.

Lower limb exoskeleton robotic devices on the other hand, have become increasingly popular over the past few years. These robotic devices are designed to provide both walking assistance and body weight support, which is the combination of the PT, OT, and orthotics approaches. Previous studies reported positive therapeutic effects of robot-assisted gait training of stroke patients, for instance; improvements in walking independence, functional walking ability, muscle activation, walking speed, muscle tone, and range of motion.

Although research has shown that the use of robotic training systems can enhance the mobility of the patients and facilitate the rehabilitation progress most of the existing devices are mainly designed to move both legs, limited to treadmill use, lack of active human-robot interaction, limited to pre-programmed walking trajectory, missing intuitive adjustment to the walking environment, and voluntary residual motor intention is seldom involved in these systems.

However, stroke patients and persons with knee problems are only affected on one leg, which has still residual motor functions, while the unaffected leg supports the body weight and help to maintain balance. The main problem of persons who sustained a stroke is the lack of knee control during the gait cycle, due to the muscle weakness in the quadriceps and hamstring muscles and the hyperextension in the knee joint. The exoskeleton robotic knee system is designed to be lightweight, has the ability to be applied on unilateral side and fully adapt the movement of the device to the patient's activity (stairs climbing, sit-to-stand).

SUMMARY OF THE INVENTION

The interactive exoskeleton robotic knee system is able to adjust to different walking conditions such as: over-ground walking, stair ascent, stair descent, sit-to-stand, slope and different walking speeds. The system is designed and configured as an exoskeleton framework to fit on the affected side of the lower limb of the user. Actuation of the exoskeleton is provided by an electric servo motor, and stability by a mechanical knee lock. The aforementioned system is capable of: (1) sensing the kinematic and kinetic gait pattern of the user using sensors on the affected leg, (2) detecting the walking intention of the user and the environmental conditions using a control algorithm based on gait analysis, and (3) driving the motorized knee joint and locking the knee joint according to a carefully adjusted gait pattern and position control to facilitate walking in different walking conditions.

According to an embodiment of the presently claimed invention, an interactive exoskeleton knee system for gait training of a user comprises: an exoskeleton framework with thigh and shank linkage on an unilateral side; a sensor system; force sensors; a motor; a mechanical lock system; a control box; a control algorithm to integrate motor and lock synchronization.

Preferably, the motor is a torque controlled servo motor. The motor aligns with a knee joint center on a lateral or a medial side of the user's leg and is operatively connected to a shank element and a thigh element of the exoskeleton framework.

Preferably, the mechanical lock system is an electromechanical lock system. The electromechanical lock system aligns with a knee joint center on a medial or lateral side of the user's leg and is operatively connected to a shank element and a thigh element.

Preferably, the system further comprises a control box with a motor control software module to automatically adjust a motor speed and an angle position to the user's walking speed and walking environment, for over ground walking, stair ascend, stair descend, slopes and sit to stand motion.

Preferably, the system further comprises a motion sensor which is attached to a thigh and/or shank of the exoskeleton framework to measure a feedback of a tilt angle and a linear level of acceleration. The force sensors are attached to a separate or connected foot piece to detect foot contact pattern during a gait cycle.

Preferably, the system further comprises a length adjustable mechanism, which allows an individual adjustment of a thigh part and a shank part of the exoskeleton framework for the user's leg.

According to an embodiment of the presently claimed invention, an interactive exoskeleton knee system comprises: an exoskeleton framework having a thigh support, a shank support; a thigh mechanical support and a shank mechanical support; at least one motion sensor mounted on the exoskeleton framework, at least one force sensor attached on a foot piece; a motor for rotating the shank mechanical support from the thigh mechanical support to generate an assistant power for a knee joint; a mechanical lock system connected the thigh mechanical support and the shank mechanical support to provide mechanical support; a control box connected with the motion sensor and the force sensor for providing power and signal communication, and sending control command to the motor and the mechanical lock system; and a control algorithm, executed by the control box, for using collected data from the motion sensor and the force sensor to detect walking intention and identify at least one walking environment based on a gait analysis, and for driving the knee joint by the motor and locking the knee joint by the mechanical lock system according to a gait pattern.

According to an embodiment of the presently claimed invention, a method for gait training of a user implemented by the system of the present invention comprises: when a loading force of the force sensor drops below a loading force threshold, an angular velocity detected by the motion sensor is larger than an angular velocity threshold, and an acceleration detected by the motion sensor is larger than an acceleration threshold, identifying a walking speed based on the control algorithm; classifying the walking environment as walking, stair ascend, or stair descend; and generating a motor control profile based on the walking speed identified.

According to an embodiment of the presently claimed invention, a method for gait training of a user implemented by the system of the present invention comprises: if the force sensor is loaded, activating knee lock and performing knee motor extension such that the user stands up and the mechanical lock system passively supports knee extension; otherwise, deactivating the knee lock and performing knee motor control to assist walking.

BRIEF DESCRIPTION OF THE DRAWINGS

Embodiments of the present invention are described in more detail hereinafter with reference to the drawings, in which.

DETAILED DESCRIPTION OF PREFERRED EMBODIMENTS

In the following description, an interactive exoskeleton knee system for gait training of a user, and the corresponding embodiments are set forth as preferred examples. It will be apparent to those skilled in the art that modifications, including additions and/or substitutions, may be made without departing from the scope and spirit of the invention. Specific details may be omitted so as not to obscure the invention; however, the disclosure is written to enable one skilled in the art to practice the teachings herein without undue experimentation.

In a first aspect, the rehabilitation system for gait training of the lower limb of a user, the system comprises:

A support structure, such as an exoskeleton framework, which can be attached to the affected lower limb of the user. The supporting structures align with the anatomical structure (e.g. shank and thigh segments) and is moveably mounted on the user's leg. The system may be adjustable to fit different leg circumference and length, by adjusting the linkages of exoskeleton framework and/or the attached straps.

The drive mechanism for the joint utilizes can be an electrically operated motor (e.g. fixated in alignment with the users knee joint). The rotary motion from the motor can be along the joint axis to support movement during walking Optional a gear assembly can be used to achieve the desired movement.

A mechanical lock ensures stability and efficient locomotion. The mechanical lock can be powered by electrical signals and installed in direct or indirect alignment with the electrically operated motor on the exoskeleton framework (e.g. medial or lateral of the target joint). The system can connect the thigh and shank part on the medial or lateral side of the device.

In a second aspect, the rehabilitation system for gait training provides sensors to identify different walking environments, comprising:

Motion sensors can be placed on the thigh, shank or foot part of the exoskeleton to identify characteristics of the gait pattern. The sensors can be joint angle sensors, gyroscope or accelerometer. This data will be collected during the gait cycle.

Force sensors can be placed on a separate foot piece or inside of the shoe of the user. One sensor may be placed on the heel area to detect the initial contact timing, another sensor can be placed on the forefoot area to detect the toe-off timing.

In a third aspect, the rehabilitation system for gait training provides a control algorithm to synchronize the usage of the electrically operated motor and the mechanical lock system and identify different walking conditions.

Control algorithm, which is able to use the collected data from the gyroscope and accelerometer to predict the walking speed, step length, sit-to-stand and the intention for each new gait cycle.

Figure 1:
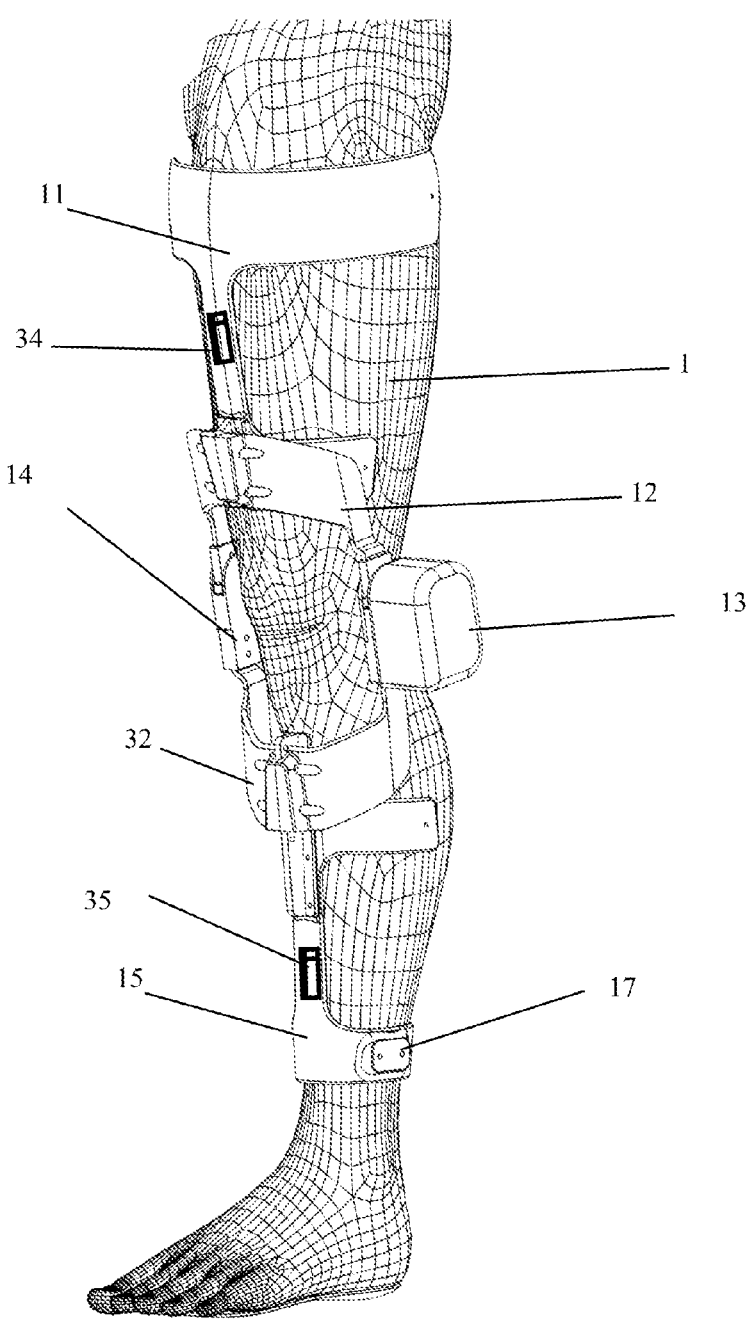
FIG. 1 is a side view of the exoskeleton device wears on a leg in accordance with a preferred embodiment of the present invention.
Figure 2:
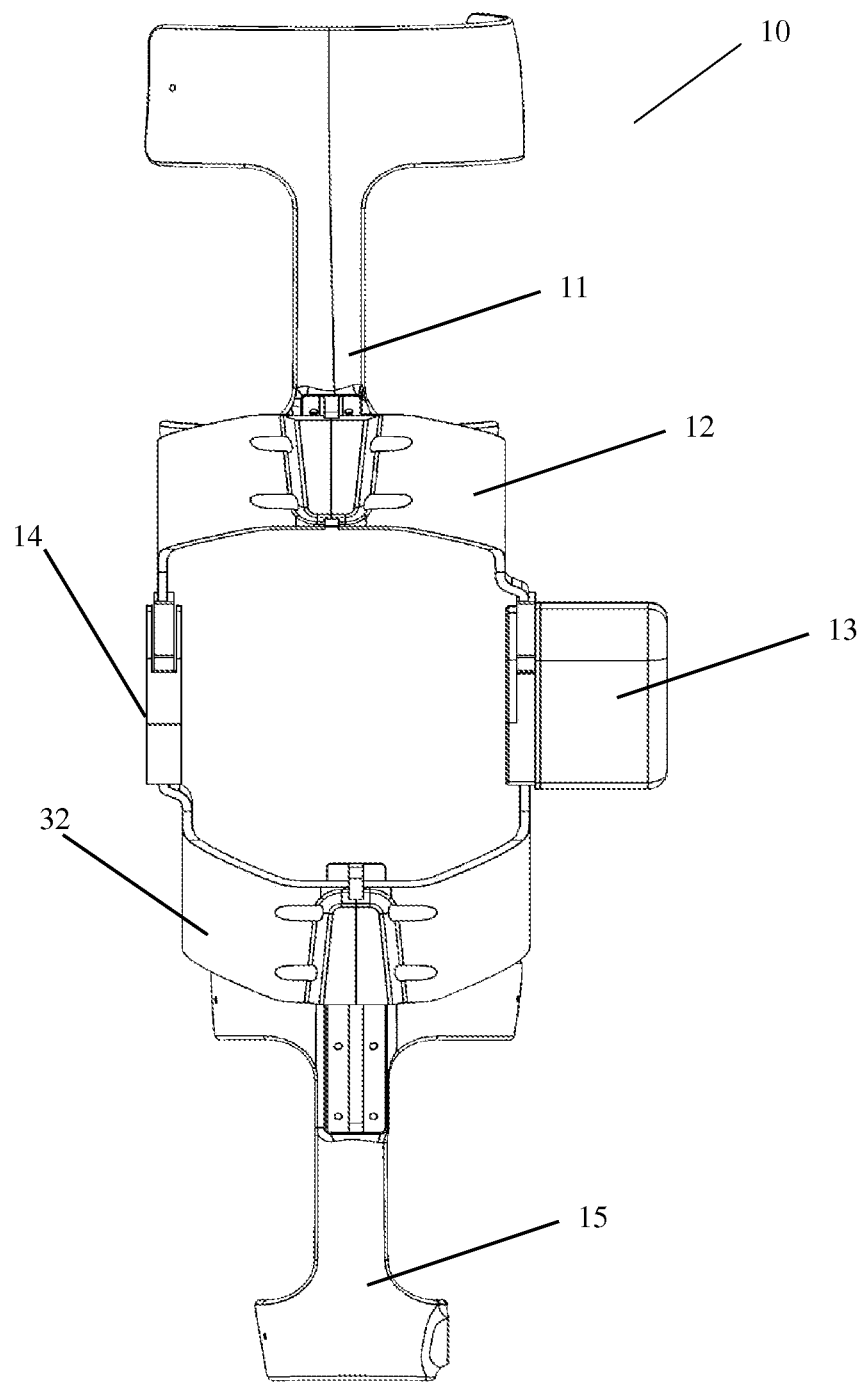
FIG. 2 is a front view of the exoskeleton device in accordance with a preferred embodiment of the present invention.
Figure 3:
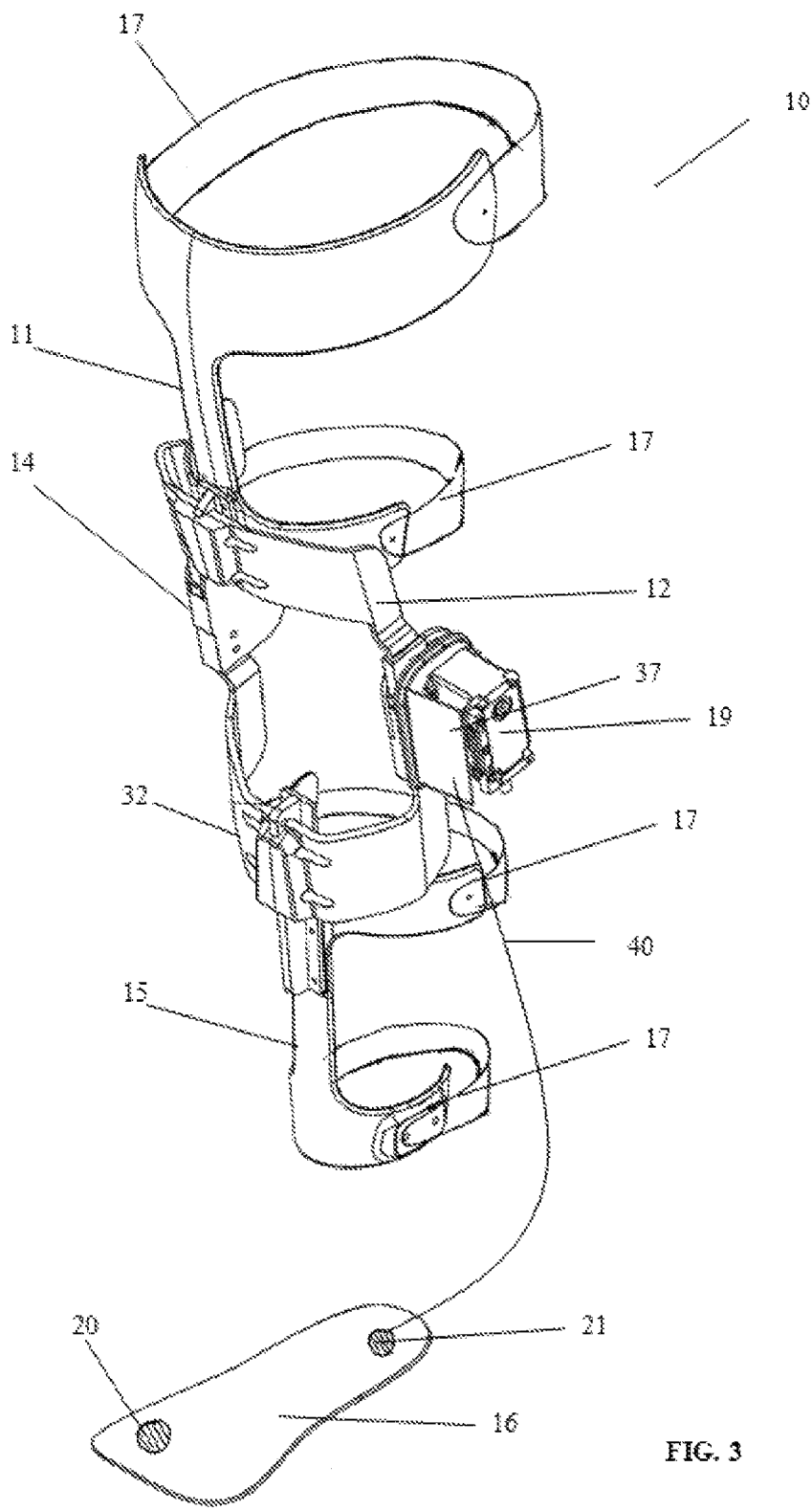
FIG. 3 is a side view of the exoskeleton device of FIG. 1 indicating the location of the motor and lock system and foot piece.
Figure 4:
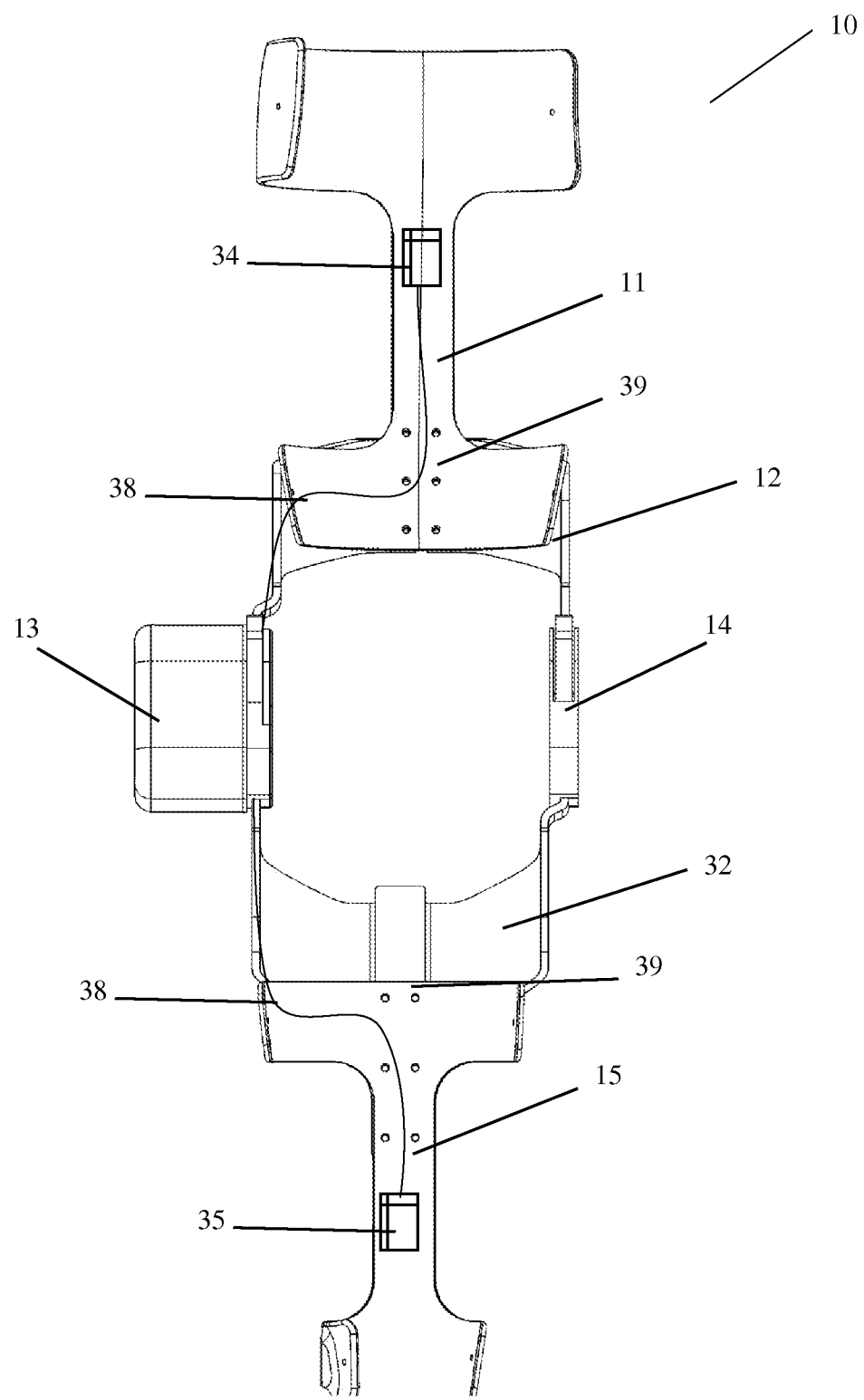
FIG. 4 is a back view of the exoskeleton device of FIG. 1.
Figure 5:
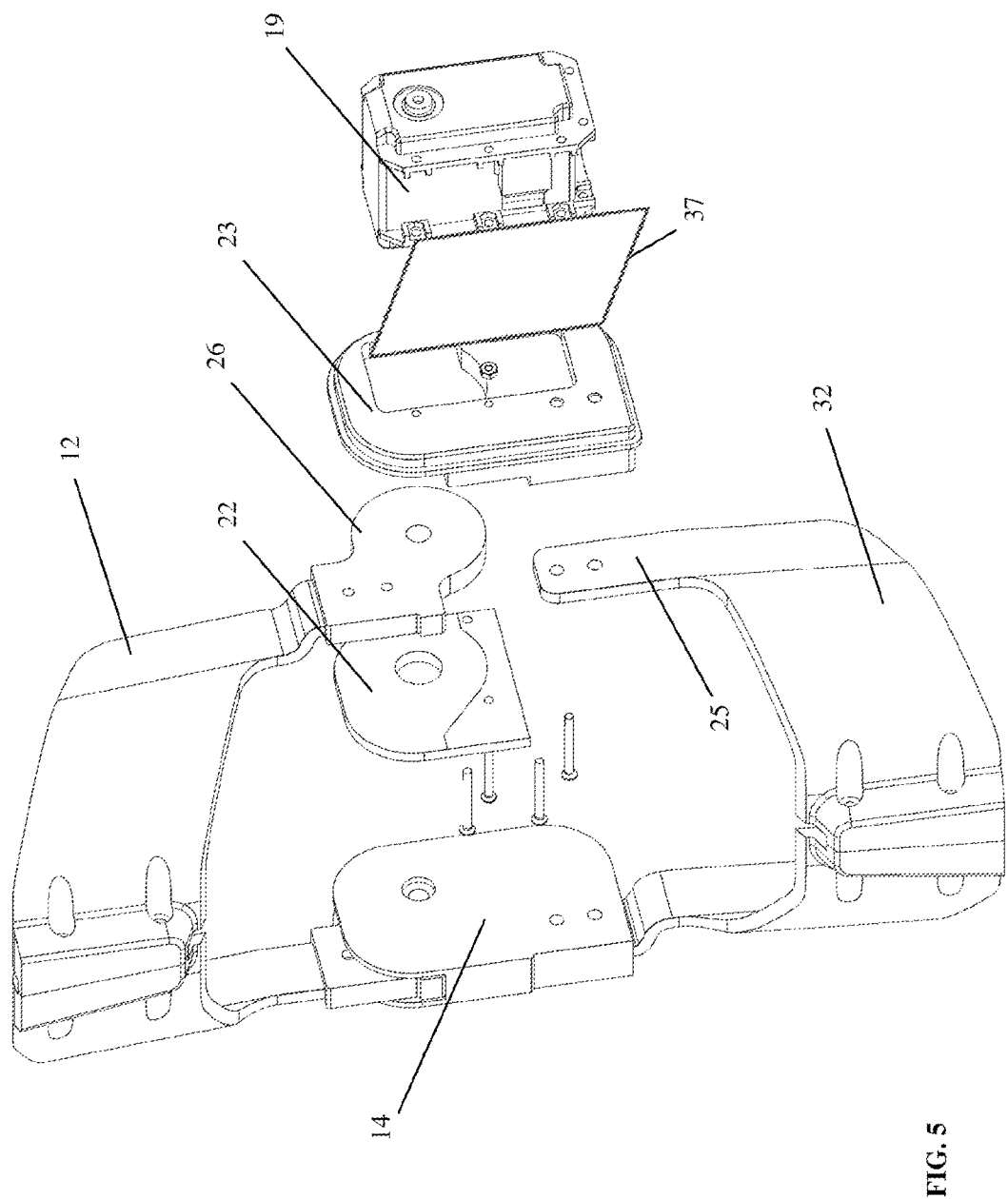
FIG. 5 is an exploded view of the linkage system to connect shank and thigh.
Figure 6:
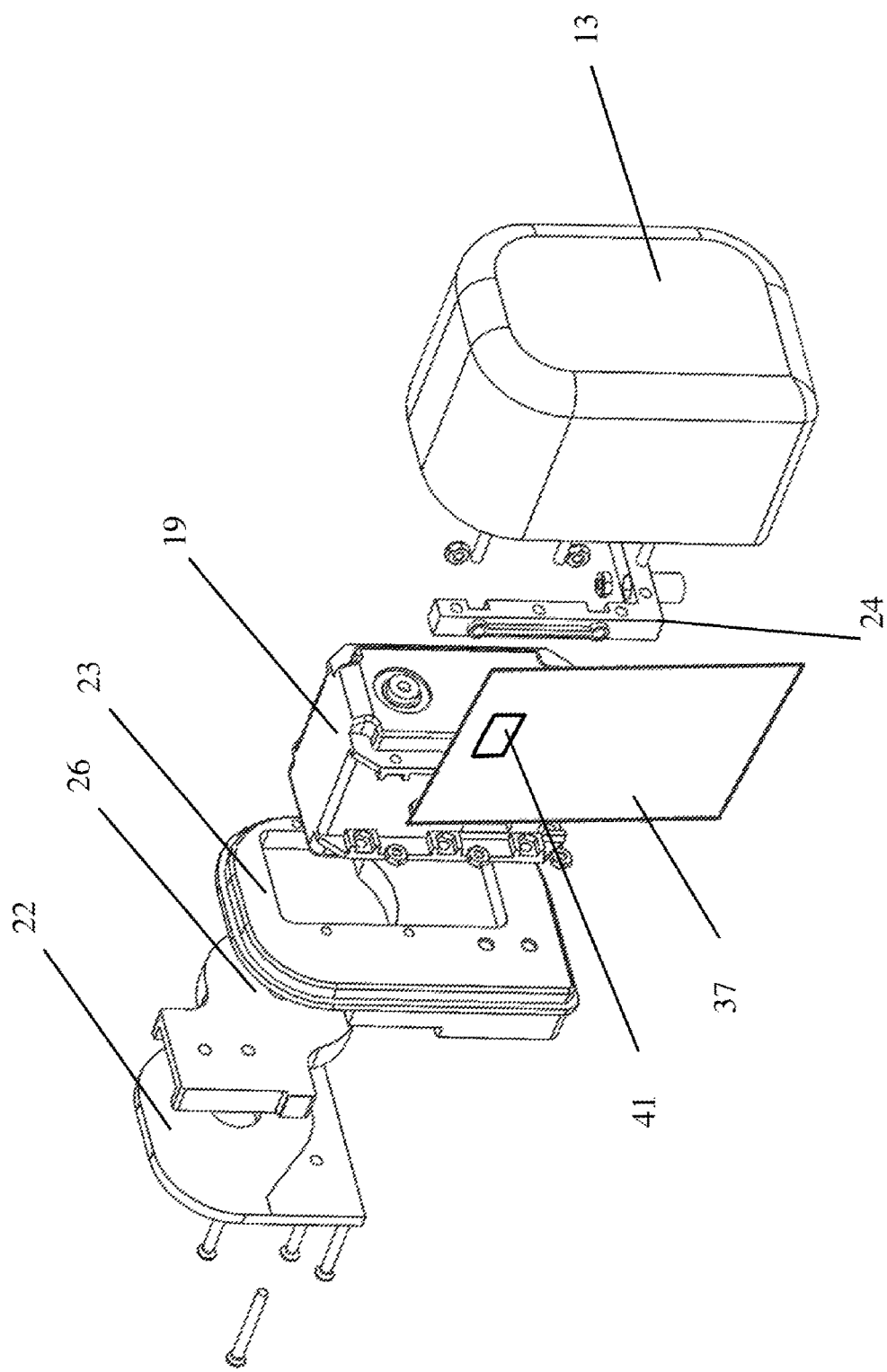
FIG. 6 is an exploded view of the motor control box cover of the exoskeleton device.
Figure 7:
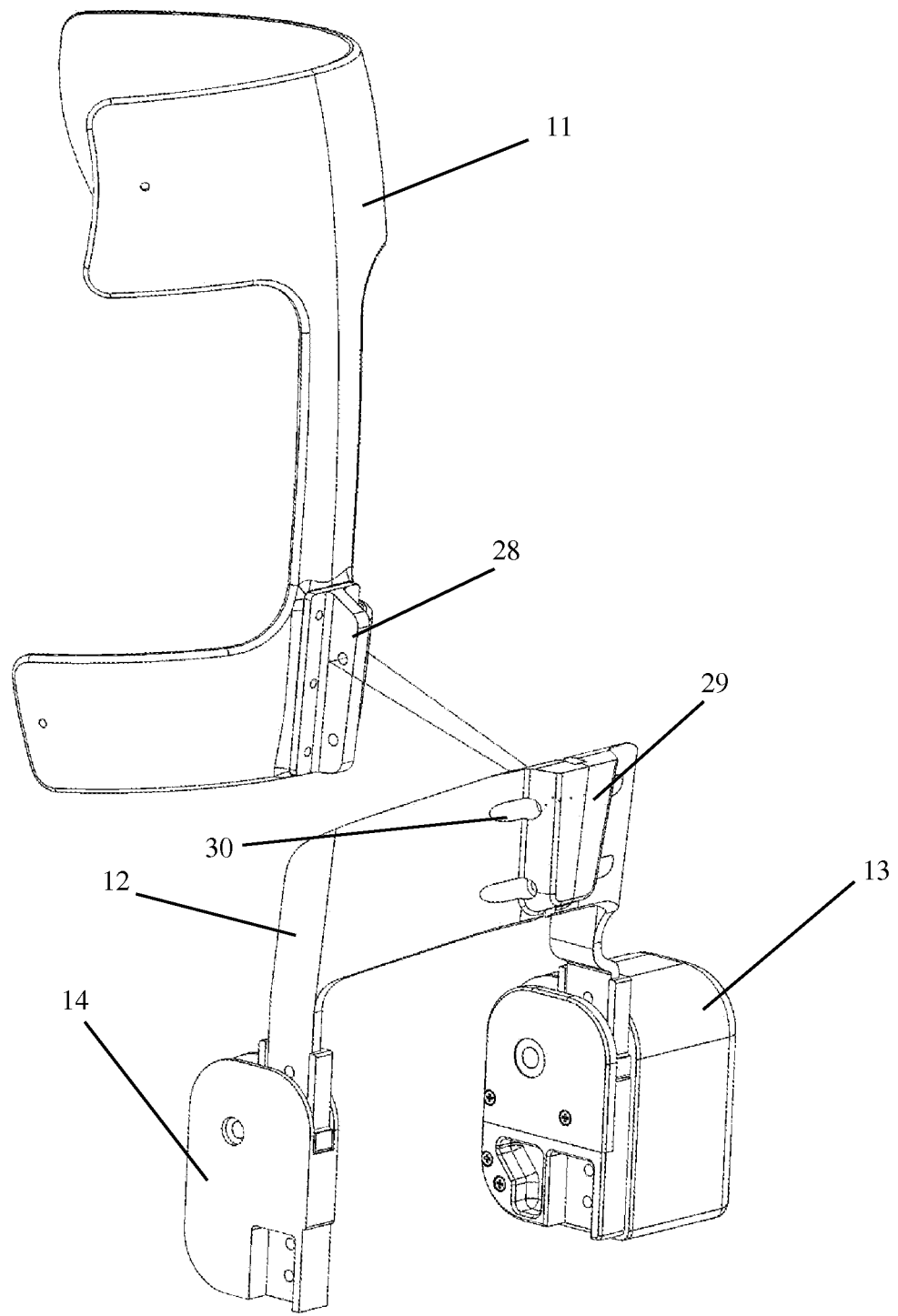
FIG. 7 is a side view of the exoskeleton knee system with separation of the linkage system and the thigh part.
Figure 8:
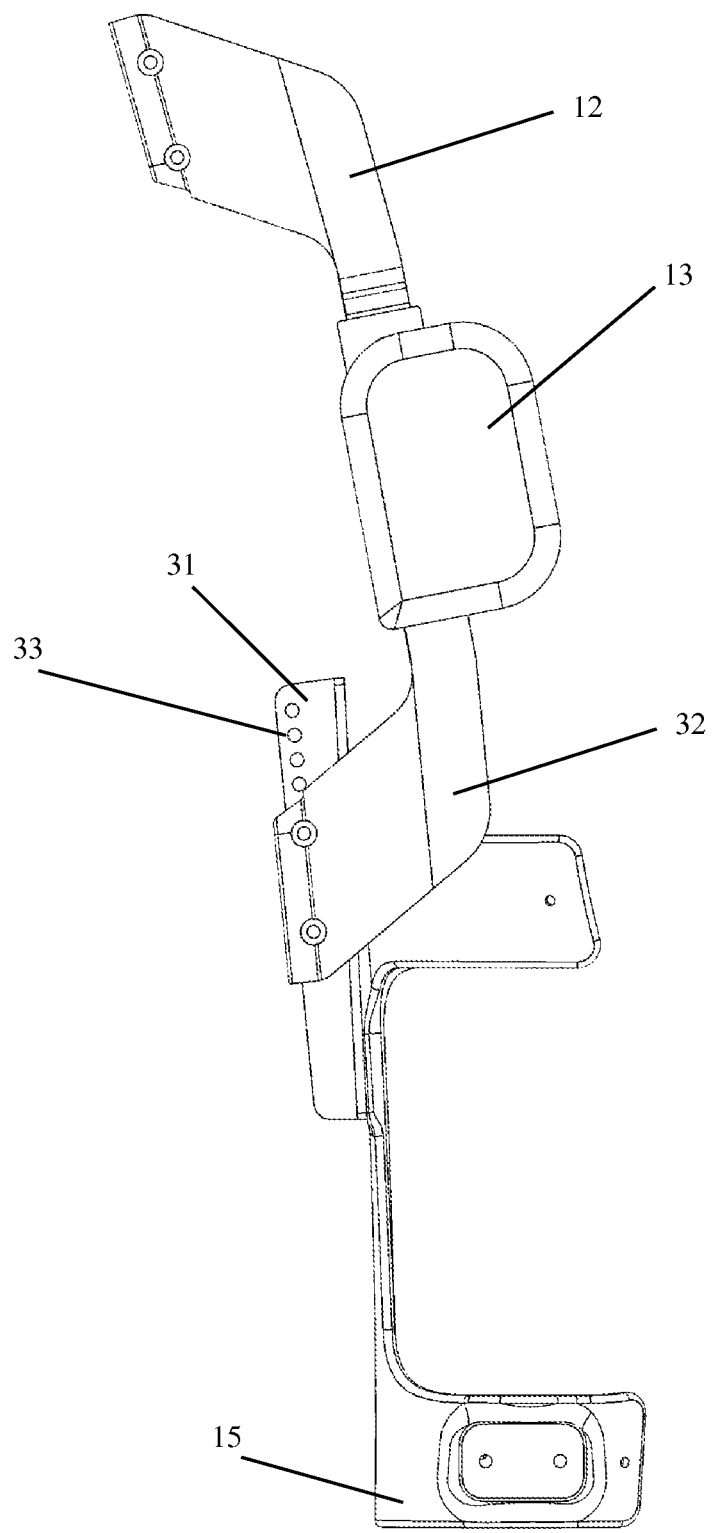
FIG. 8 shows the adjustment of the thigh part to different leg lengths.
Figure 9:
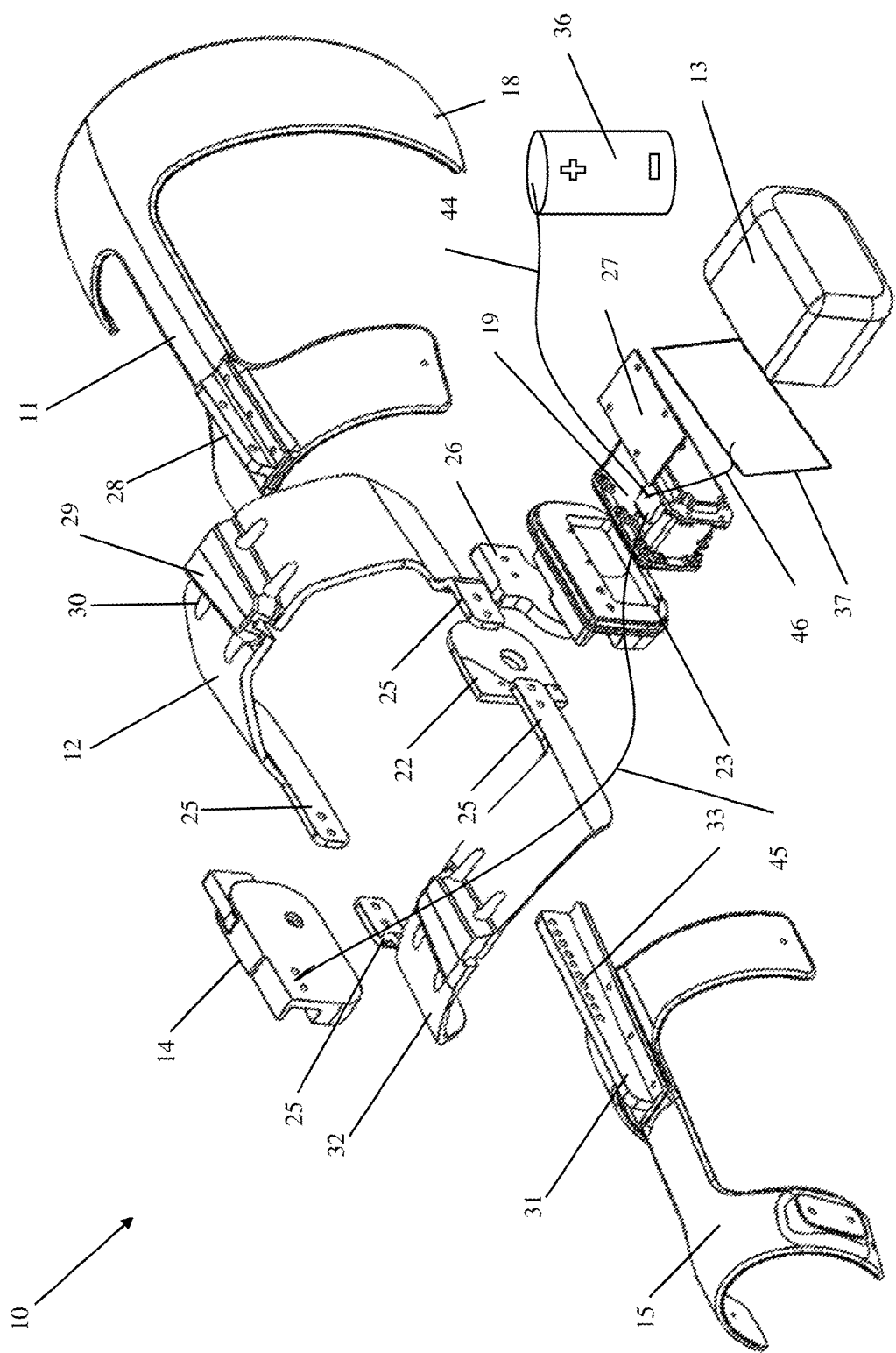
FIG. 9 shows the exploded view of the exoskeleton device of FIG. 1.
Figure 10:
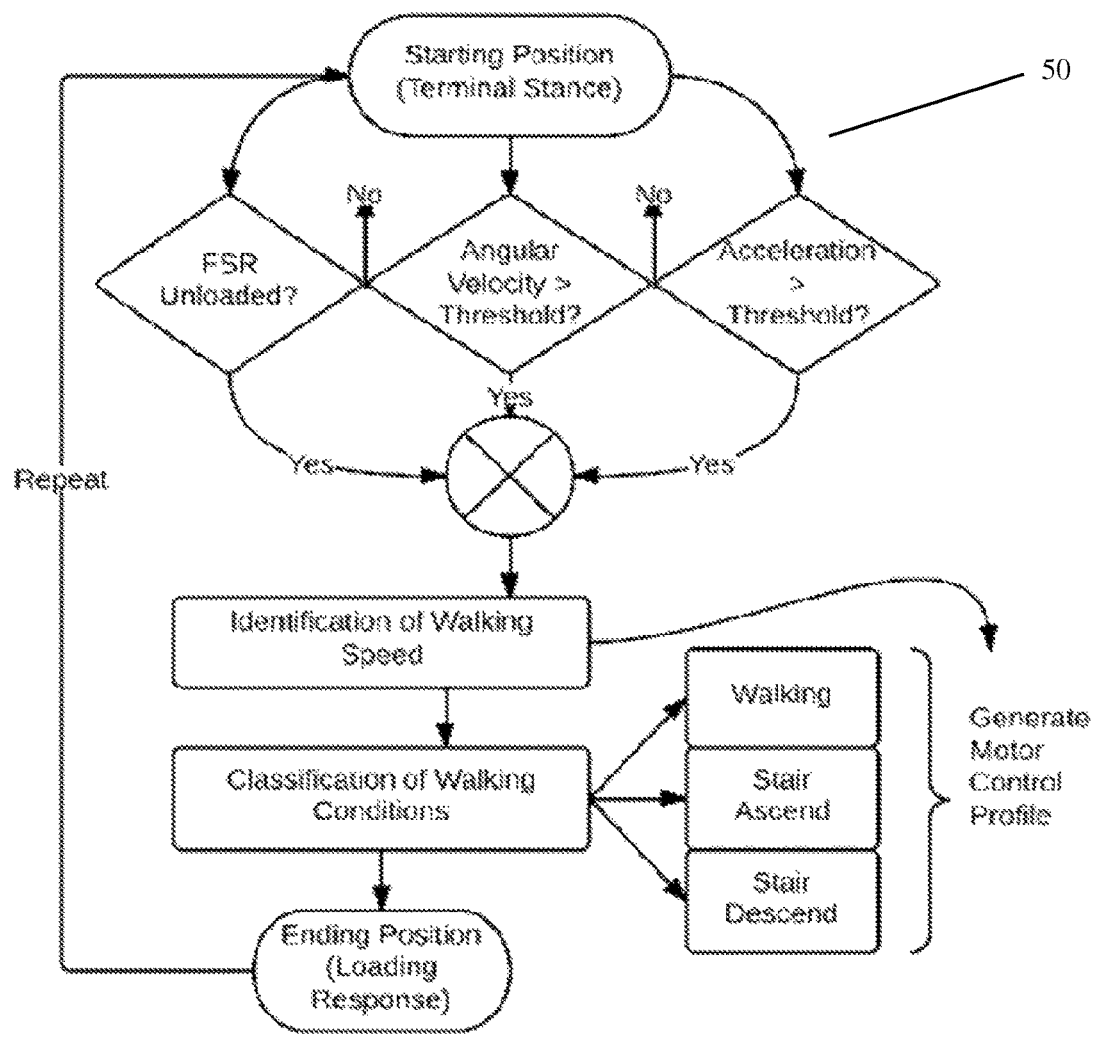
FIG. 10 is a process flow diagram of the control algorithm to identify different walking environments.

Control algorithm to identify different environments (over ground walking, stair ascent, stair descent). FIG. 10 describes an example of the control algorithm in detail: The user has to lift the robotic leg up from the ground, i.e. shifting body weight on the contralateral leg. When the loading force of force sensor drops below a certain threshold, it suggests the beginning of pre-swing phase. Walking speed will be determined by the kinematic or kinetic gait pattern obtained from the sensor on the robotic knee system. For example, if the forward angular velocity and acceleration exceeds the thresholds, the swing phase will be triggered. The swing phase consists of two major events: (1) knee flexion and (2) knee extension. Motor driven torque level and timing will be determined from the maximum joint torque and spatial-temporal features obtained from calibration templates of knee joint angles during swing phase. Eventually, if force sensor is loaded, it suggests loading response and the end of swing phase. The control algorithm will repeat afterward until user stops swinging the leg at pre-swing phase, i.e. leg angular velocity below threshold. If the user is in sitting position, the user has to shift the body weight towards the robotic knee system and maintain a loading force on the force sensors. The sensors will acquire the loading pattern and the standing gesture will be detected. The knee joint will then progressively extend during the standing motion and the knee lock will support the standing position by preventing a knee flexion. At all time, the knee joint will be locked as long as the robotic knee system is loaded, i.e. user is standing or during the stance phase.

Figure 12:
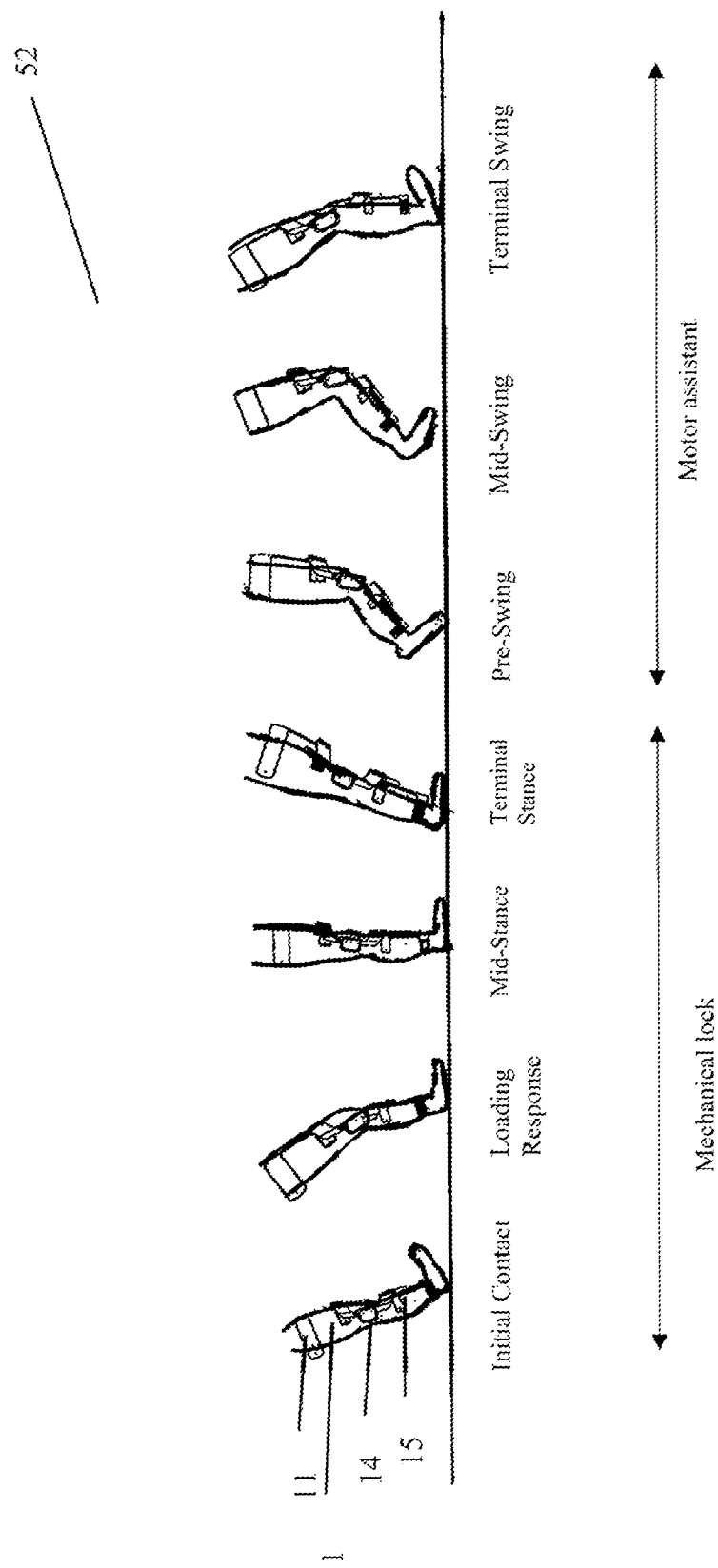
FIG. 12 is a diagram of the lock and motor control during one gait cycle.

The mechanical lock ensures stability of the knee joint during standing and the stance phase by supporting the body weight and preventing a hyperextension of the knee. The knee joint will be locked at the initial contact and throughout the loading response until the completion of the terminal stance phase. If the foot is lifted up from the ground the mechanical lock will be unlocked to enable the swing phase. The mechanism of the activation of the mechanical knee lock system is illustrated in FIG. 12.

Figure 11:
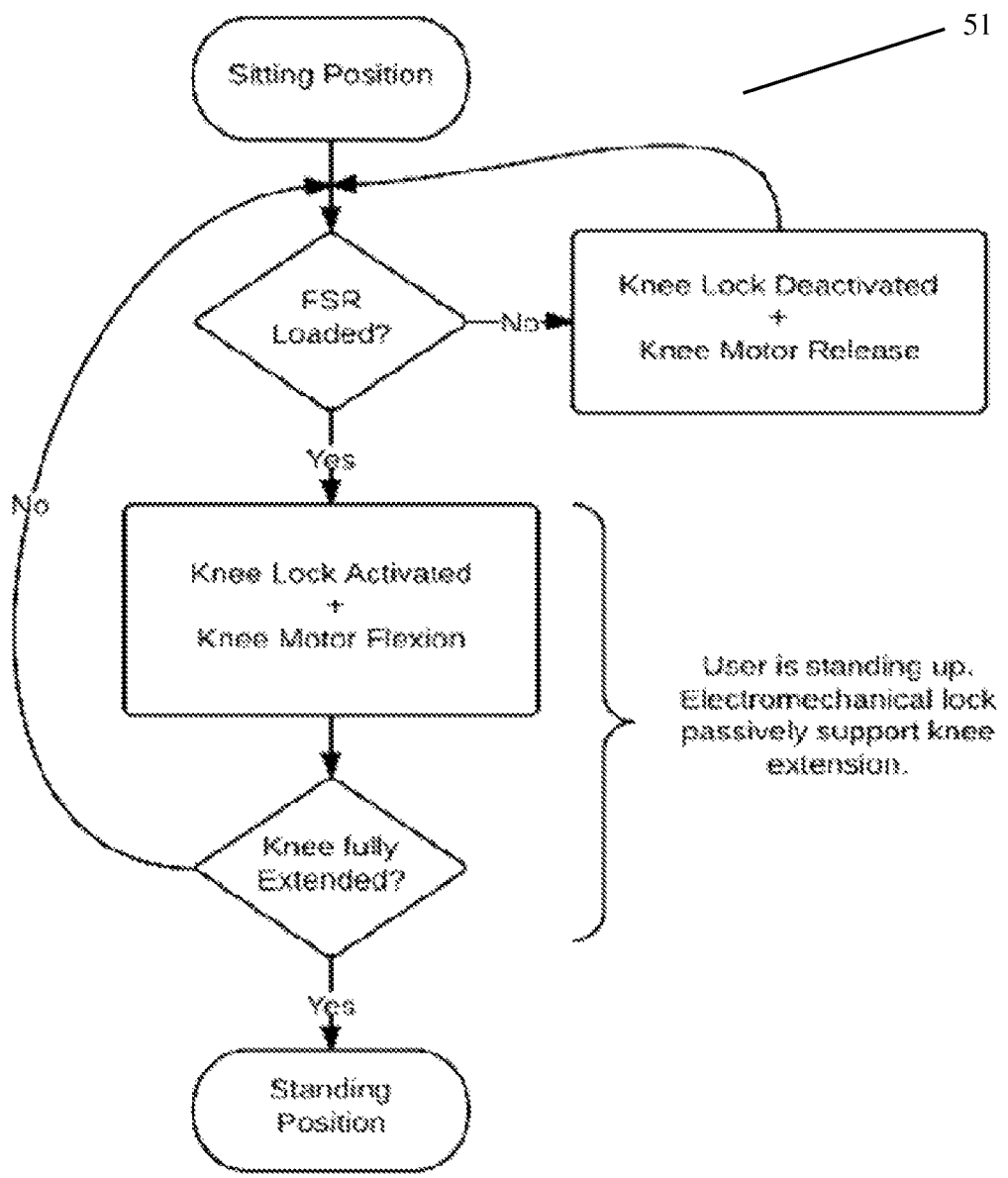
FIG. 11 is a process flow diagram of the control algorithm for controlling the sit to stand motion.

For the sit-to-stand mode, FIG. 11 shows an example of the control algorithm. The user has to shift the bodyweight on the entire foot, which will activate the knee lock. The design of the knee lock allows a step by step lock system until the knee joint is fully extended. Once the patient reaches the end position (standing) the lock will be activated until the patient reaches the terminal swing phase (heel-off). The knee lock will be than again activated once the patient reaches the beginning of the stance phase (initial contact) or is just standing.

Control algorithm for adjustable level of support allows the user an individual level of assistance throughout the usage of the device. The level of assistance has a range from 0-100%, while 0% is equal to no power assistance, conversely 100% means maximal assistance of the servomotor (which may be 60 Nm) and minimal voluntary intention of the user.

Referring to FIGS. 1 to 12, an embodiment of an interactive exoskeleton robotic knee system 10 is provided that is driven by voluntary intention of the user. Suitable users include people with neurological diseases with motor disabilities in the lower extremity, patients with knee problem and people with muscle weakness.

Preferred embodiment of this invention will now be discussed in detail with respect to the drawings. The drawings include schematic figures that may not be to scale, which will be fully understood by skilled artisans with reference to the accompanying description.

The embodiment of this invention is the interactive exoskeleton robotic knee system 10 that has a compact and lightweight structure. Carbon fiber composites, fiber reinforced thermosetting plastic such as high-density polycarbon, and lightweight metals such as aluminum and titanium are non-limiting candidates of material that can be used to fabricate the interactive exoskeleton robotic knee system 10.

The interactive exoskeleton robotic knee system 10 is attached on the affected side of the user's leg 1 with the thigh support 11 and distal shank support 15. Adjustable straps 17 are attached on both thigh support 11 and distal shank support 15 to secure the position of the interactive robotic knee system 10 on the leg 1 and to align the knee joint center with rotational axis of the mechanical lock system 14 and motor 19. Thigh mechanical support 12 and shank mechanical support 32 are connected with the mechanical lock system 14 and motor 19 to provide mechanical support.

Motion sensor on thigh 34 is mounted on the thigh support 11 and motion sensor on shank 35 is mounted on the distal shank support 15. Motion sensor on thigh 34 and motion sensor on shank 35 are connected with a connection cable 38 from the sensor to the control box 37 to provide power and signal communication. Force sensor for forefoot 20 and force sensor for heel 21 attached on the foot piece 16, with a foot connection cable 40 from the force sensors to the control box 37 to provide power and signal communication. Wireless communication unit 41 on control box 37 can send and receive command to other electronic device for data collection and control.

The mechanical connector for the motor base to the thigh rotation base 22 is connected with the motor base 23 for mounting the motor 19 on the thigh rotation base 26. The motor 19 is fixed on the motor base 23 which connected with the motor connection bar 25 to rotate the shank mechanical support 32 from the thigh mechanical support 12 to generate assistant power for the knee joint. The control box 37 send control command to the motor 19 and the mechanical lock system 14. A mounting bar 24 is used to attach the motor 19 to the motor base 24 and motor control box cover 13.

The thigh support 11 has a proximal connector 28 to be connected with the distal connector 29 with a thigh screw system 30 for the length adjustment for fitting the thigh length. The distal shank support 15 has an adjustment bar 31 to be connected with the shank mechanical support 32, and the shank length is adjusted by length adjustable mechanism 33.

A power source 36 supplies power to the control box 37, the mechanical lock system 14 and motor 19. They are connected with power source cable 44, mechanical lock power and control cable 45, and control box power and control signal cable 46 respectively. Stabilizer 27 is to protect the motor 19 and the control box 37, which is housed inside the motor control box cover 13.

The control box 37 executes the control profile for walking 50 in a gait cycle 52, and sit-to-stand profile 51 based on the sensor signals.

The present invention is applicable to facilitation of gait rehabilitation, stroke rehabilitation, post knee injury rehabilitation, geriatric recurvatum rehabilitation and prevention, body weight support, muscle strengthening, outdoor/indoor application. The present invention is also able to be implemented in hospital, rehabilitation clinics, elderly centers.

The foregoing description of the present invention has been provided for the purposes of illustration and description. It is not intended to be exhaustive or to limit the invention to the precise forms disclosed. Many modifications and variations will be apparent to the practitioner skilled in the art.

The embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the following claims and their equivalence.

What is claimed is:

1. An interactive exoskeleton knee system comprising:
    an exoskeleton framework having a thigh support, a shank support, a thigh mechanical support and a shank mechanical support;
    at least one motion sensor mounted on the exoskeleton framework;
    at least one force sensor attached on a foot piece or inside of a shoe;
    a motor for rotating the shank mechanical support from the thigh mechanical support to generate an assistant power for a knee joint;
    a mechanical lock system connected the thigh mechanical support and the shank mechanical support to provide mechanical support;
    a control box connected with the at least one motion sensor and the at least one force sensor for providing power and signal communication, and sending control command to the motor and the mechanical lock system; and
    a control algorithm, executed by the control box, for using collected data from the at least one motion sensor and the at least one force sensor to identify a walking environment based on a gait analysis, and for driving the knee joint by the motor and locking the knee joint by the mechanical lock system according to a gait pattern based on the walking environment;
    wherein the at least one motion sensor comprises a gyroscope and an accelerometer, and the control algorithm is further for using data detected by the at least one motion sensor for identifying a walking speed; and
    wherein the control algorithm is further used for identifying the walking speed when a loading force detected by the at least one force sensor drops below a loading force threshold, an angular velocity detected by the gyroscope is larger than an angular velocity threshold, and an acceleration detected by the accelerometer is larger than an acceleration threshold, and classifying the walking environment.

2. The interactive exoskeleton knee system according to claim 1, wherein the motor aligns with a knee joint center on a lateral or a medial side of a user's leg.

3. The interactive exoskeleton knee system according to claim 1, wherein the mechanical lock system aligns with a knee joint center on a lateral or a medial side of a user's leg.

4. The interactive exoskeleton knee system according to claim 1, wherein the at least one force sensor is placed on a heel area of the foot piece or the inside of the shoe to detect initial contact timing, or is placed on a forefoot area of the foot piece or the inside of the shoe to detect toe-off timing.

5. The interactive exoskeleton knee system according to claim 1, wherein the walking environment is over-ground walking, stair ascend, stair descend, slopes or sit-to-stand motion.

6. The interactive exoskeleton knee system according to claim 1, further comprising a length adjustable mechanism allowing an individual adjustment of the thigh support and the shank support.

7. A method for gait training of a user implemented by the interactive exoskeleton knee system of claim 1, the method comprising:
    when a loading force detected by the at least one force sensor drops below a loading force threshold, an angular velocity detected by the gyroscope is larger than an angular velocity threshold, and an acceleration detected by the accelerometer is larger than an acceleration threshold, identifying the walking speed based on the control algorithm;
    classifying the walking environment as walking, stair ascend, or stair descend based on the gait analysis; and
    generating a motor control profile based on the walking speed identified.

8. A method for gait training of a user implemented by the interactive exoskeleton knee system of claim 1, the method comprising:
    if the at least one force sensor is loaded,
        activating knee lock and performing knee motor extension such that the user stands up and the mechanical lock system passively supports knee extension;
        otherwise, deactivating the knee lock and performing knee motor control to assist walking.

9. The interactive exoskeleton knee system according to claim 1, wherein the motor is a torque controlled servo motor.

10. The interactive exoskeleton knee system according to claim 1, wherein the mechanical lock system is an electromechanical lock system.

11. The interactive exoskeleton knee system according to claim 1, further comprising an external or internal power supply which is located within the control box.

12. The interactive exoskeleton knee system according to claim 1, wherein the at least one motion sensor is attached to the thigh support or the shank support of the exoskeleton framework.

13. The interactive exoskeleton knee system according to claim 1, wherein the at least one force sensor detects a foot contact pattern during a gait cycle.

14. The interactive exoskeleton knee system according to claim 1, further comprising a wireless control system.

15. The interactive exoskeleton knee system according to claim 1, wherein the mechanical lock system is for locking the knee joint during a stance phase and unlocking the knee joint during a swing phase.

16. A method for gait training of a user implemented by an interactive exoskeleton knee system, the interactive exoskeleton knee system comprising:
- an exoskeleton framework having a thigh support, a shank support, a thigh mechanical support and a shank mechanical support;
- at least one motion sensor mounted on the exoskeleton framework;
- at least one force sensor attached on a foot piece or inside of a shoe;
- a motor for rotating the shank mechanical support from the thigh mechanical support to generate an assistant power for a knee joint;
- a mechanical lock system connected the thigh mechanical support and the shank mechanical support to provide mechanical support;
- a control box connected with the at least one motion sensor and the at least one force sensor for providing power and signal communication, and sending control command to the motor and the mechanical lock system; and
- a control algorithm, executed by the control box, for using collected data from the at least one motion sensor and the at least one force sensor to identify a walking environment based on a gait analysis, and for driving the knee joint by the motor and locking the knee joint by the mechanical lock system according to a gait pattern based on the walking environment;
- wherein the at least one motion sensor comprises a gyroscope and an accelerometer, and the control algorithm is further for using data detected by the at least one motion sensor for identifying a walking speed;

the method comprising:
- when a loading force detected by the at least one force sensor drops below a loading force threshold, an angular velocity detected by the gyroscope is larger than an angular velocity threshold, and an acceleration detected by the accelerometer is larger than an acceleration threshold, identifying the walking speed based on the control algorithm;
- classifying the walking environment as walking, stair ascend, or stair descend based on the gait analysis; and
- generating a motor control profile based on the walking speed identified.

* * * * *